(12) United States Patent
Marchini

(10) Patent No.: US 12,310,889 B2
(45) Date of Patent: May 27, 2025

(54) CAPSULOTOMY DEVICE AND METHOD

(71) Applicant: Enrico Marchini, Verona (IT)

(72) Inventor: Enrico Marchini, Verona (IT)

(73) Assignee: HORUS MEDTECH S.r.l, Verona (IT)

(*) Notice: Subject to any disclaimer, the term of this patent is extended or adjusted under 35 U.S.C. 154(b) by 968 days.

(21) Appl. No.: 17/292,970

(22) PCT Filed: Nov. 5, 2019

(86) PCT No.: PCT/EP2019/080287
§ 371 (c)(1),
(2) Date: May 11, 2021

(87) PCT Pub. No.: WO2020/099192
PCT Pub. Date: May 22, 2020

(65) Prior Publication Data
US 2022/0000665 A1    Jan. 6, 2022

(30) Foreign Application Priority Data

Nov. 15, 2018  (IT) .......................... 102018000010363

(51) Int. Cl.
*A61F 9/007*        (2006.01)
(52) U.S. Cl.
CPC ...... *A61F 9/00754* (2013.01); *A61F 9/00763* (2013.01); *A61F 2210/0014* (2013.01); *A61F 2230/0006* (2013.01)
(58) Field of Classification Search
CPC .............. A61F 9/00754; A61F 9/00763; A61F 2210/0014; A61F 2230/0006; A61F 9/013; A61B 17/142; A61B 17/144; A61B 17/147; A61B 17/149
See application file for complete search history.

(56) References Cited

U.S. PATENT DOCUMENTS

| 6,165,190 | A | 12/2000 | Nguyen |
| 8,075,578 | B2 | 12/2011 | Deli et al. |
| 2013/0066351 | A1 | 3/2013 | Giardina et al. |
| 2015/0216728 | A1 | 8/2015 | Keller |

FOREIGN PATENT DOCUMENTS

| DE | 4012882 | 10/1991 | |
| DE | 4012882 A1 * | 10/1991 | ............. A61F 9/013 |
| DE | 197 19 549 | 11/1998 | |
| WO | 2009/153550 | 12/2009 | |
| WO | 2011/155922 | 12/2011 | |
| WO | 2014/145919 | 9/2014 | |
| WO | 2015/166394 | 11/2015 | |
| WO | 2017/199217 | 11/2017 | |
| WO | WO-2017199217 A1 * | 11/2017 | ......... A61F 9/00754 |

* cited by examiner

*Primary Examiner* — Ashley L Fishback
*Assistant Examiner* — Chima U Igboko
(74) *Attorney, Agent, or Firm* — The Law Office of Joseph L. Felber

(57) ABSTRACT

A capsulotomy device has a tool holder. The tool holder includes a cutting blade at its distal end and is arranged to move in a distal direction in the device to form an operative state of the device where the cutting blade projects out of a distal end of the capsulotomy device. The at least a portion of the tool holder is adapted in the device's operative state to reciprocate in the distal and proximal directions to urge rotation of the cutting blade.

11 Claims, 10 Drawing Sheets

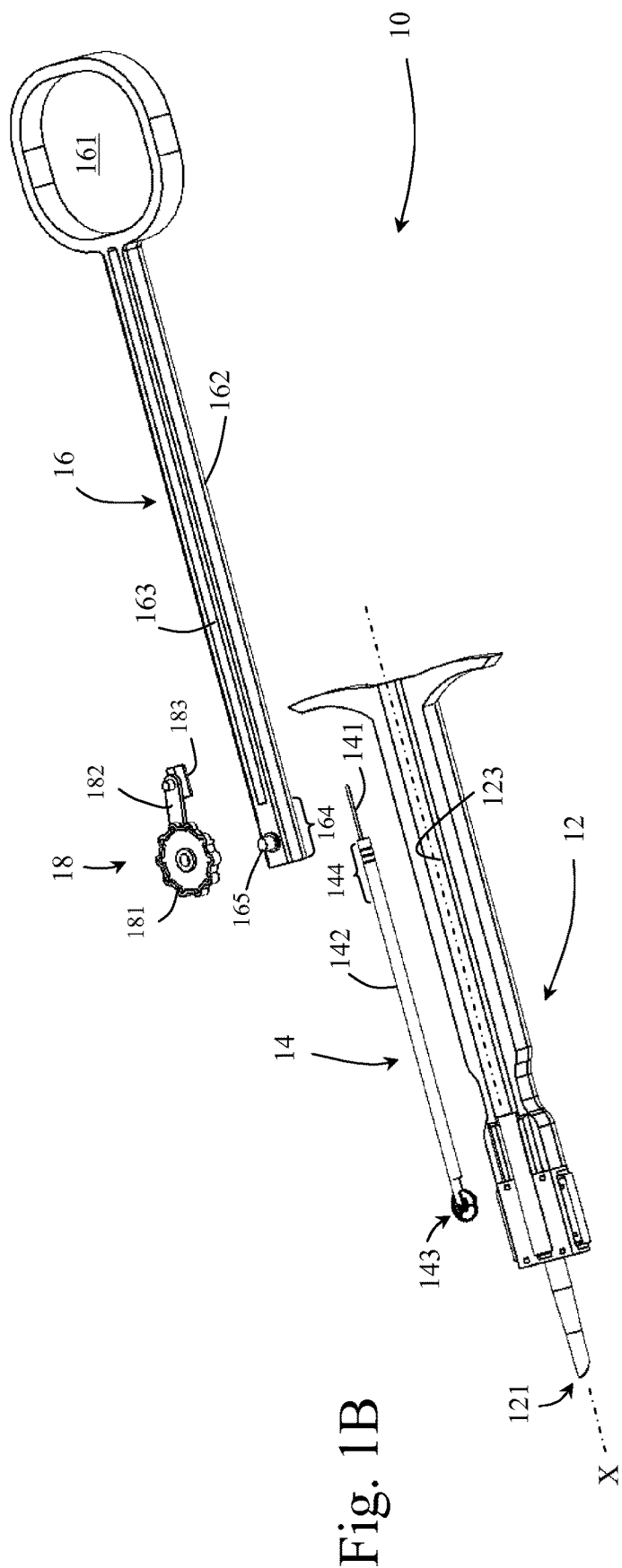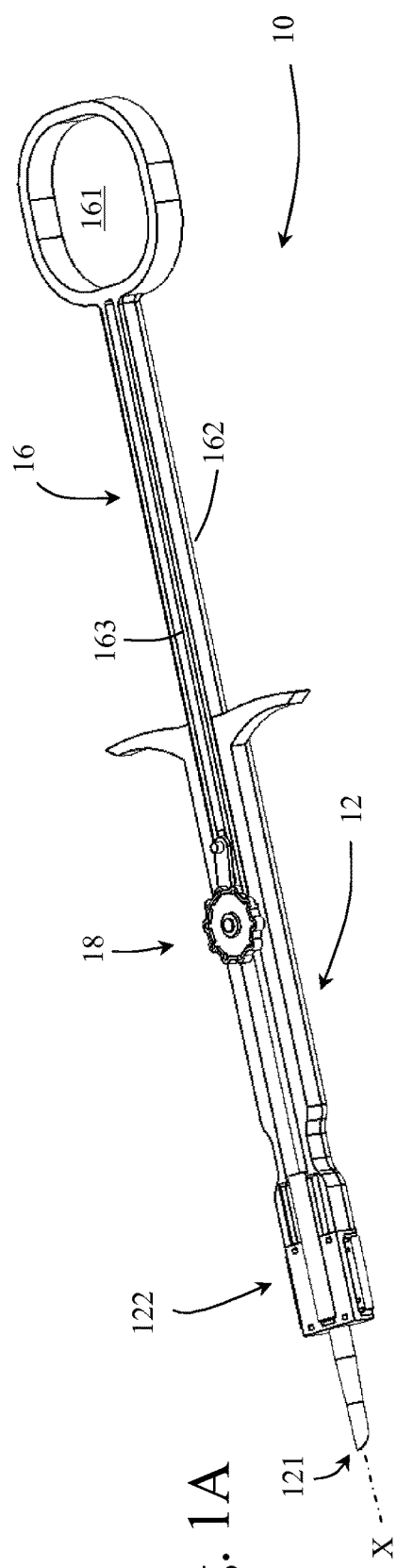
Fig. 1B
Fig. 1A

CAPSULOTOMY DEVICE AND METHOD

TECHNICAL FIELD

Embodiments of the invention relate to a capsulotomy device and method, in particular of a type comprising a cutting blade.

BACKGROUND

Capsulorhexis or Capsulotomy is a procedure that nowadays is typically used for manually removing a portion of the anterior lens capsule during cataract surgery. Once performed, the crystalline lens within the capsule may be removed, leaving the capsule in place acting as a partition between posterior and anterior portions of the eye; preventing, inter alia, the vitreous humor from moving forward. The remaining capsule may then be used for firmly housing e.g. an artificial intraocular lens.

Incisions made by a surgeon using hand-held cutting needle and forceps is a method traditionally used for forming a generally continuous aperture in the capsule through which the lens may then be removed, however formation of a smooth and continuous hole in the capsule may be formed also by dedicated cutting tools. Such tools may be suited for evenly applying cutting forces upon the capsule during surgery—in order to substantially avoid any unintentional tears in the capsule.

WO2015166394 describes, for example, a device for producing cuts or perforations on a human or animal eye in order to open the eye lens. The device operates by means of a cutting element that can be inserted into the interior of the eye and a drive device, which is arranged outside of the eye, in order to cause mechanical, in particular oscillatory vibrations or rotation of the cutting element in the interior of the eye.

DE4012882 in another example describes a surgical instrument for operating on a cataract of the eye that has a hollow handle which receives the blade holder. The blade is made from a flat strip of flexible material which is bent to form a ring and the ring is gripped between a roller inside the ring and two rollers outside the ring. A drive mechanism inside the handle rotates the rollers which cause the ring to rotate so that its edge cuts out the cataract.

WO2014145919 in yet a further example describes a device for performing an anterior capsulotomy procedure. The device includes a body having proximal and distal end and a cutting element having at least one surgical blade rotatably disposed on a distal end of the body. The cutting element is attached to a pinion including a plurality of gear teeth that intermesh to cause rotation in the pinion.

SUMMARY

The following embodiments and aspects thereof are described and illustrated in conjunction with systems, tools and methods which are meant to be exemplary and illustrative, not limiting in scope.

In an embodiment there is provided a capsulotomy device comprising a tool holder, the tool holder comprising a circular cutting blade at its distal end and being arranged to move in a distal direction in the device to form an operative state of the device where the cutting blade projects out of a distal end of the capsulotomy device, wherein at least a portion of the tool holder is adapted in the device's operative state to reciprocate in the distal and proximal directions to urge oscillating rotation of the cutting blade.

Said reciprocating portion of the tool holder may be in the form of an axially extending rod that may be arranged to connect/mate at its distal axial end to the cutting blade. Thus, by reciprocating axial movements of the rod, rotational oscillations of the cutting blade may be urged about a central pivot of the cutting blade, where said pivot being preferably formed by portions of the cutting blade itself.

Such embodiment where rotational oscillations may be formed by a simple mechanism including an axially extending rod—provides a solution for performing cutting actions with a relative simple mechanism that has less parts than otherwise may be required for formation of such a rotational oscillating cutting action.

In at least certain embodiments, rotational angular actions of oscillation of the cutting blade about its pivot—may be relative slight—possibly in a magnitude of about 170 degrees or less, possibly about 90 degrees or less. That is to say that the cutting blade may be rotated from a given position by about said 170, 90 or less degrees in a first rotational direction about its pivot—before oscillating back towards said given position in an opposing second rotational direction.

These rotational movements of the cutting blade may be used for cutting a portion of an anterior side of a lens capsule during e.g. cataract surgery.

In an embodiment, the capsulotomy device may comprise a piston and the tool holder being coupled to the piston at its proximal end, wherein the urging of the tool holder in the distal direction is via the piston.

The piston may be manually held by a surgeon performing surgery e.g. cataract surgery on a patient's eye, for example for manually inserting a tip region of the device via an incision formed through a cornea of the eye—prior to the device assuming its operative state.

In various embodiments, the capsulotomy device comprises a driving mechanism, either manually activated or automatically activated, for reciprocating the at least portion of the tool holder in the distal and proximal directions.

In an embodiment there is provided a cutting blade for a capsulotomy device having a unitary one-piece construction, the cutting blade comprising a circular body and a plurality of spoke members integral with the body and extending each away from different circumferential locations about the body to meet at central region of the cutting blade.

In addition to the exemplary aspects and embodiments described above, further aspects and embodiments will become apparent by reference to the figures and by study of the following detailed descriptions.

BRIEF DESCRIPTION OF THE FIGURES

Exemplary embodiments are illustrated in referenced figures. It is intended that the embodiments and figures disclosed herein are to be considered illustrative, rather than restrictive. The invention, however, both as to organization and method of operation, together with objects, features, and advantages thereof, may best be understood by reference to the following detailed description when read with the accompanying figures, in which:

FIGS. 1A and 1B schematically show assembled and exploded views, respectively, of an embodiment of a capsulotomy device in accordance with the present invention;

Figure 2A:
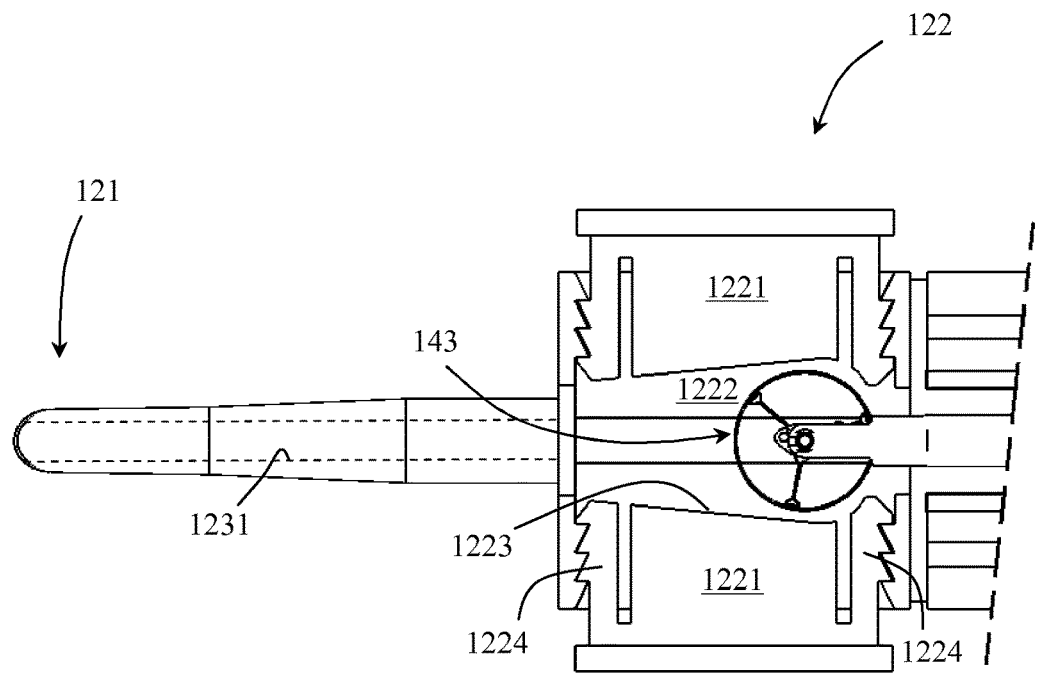
FIGS. 2A and 2B schematically show a distal position of an embodiment of a capsulotomy device in, respective, unloaded and loaded states of a cutting blade.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated within the figures to indicate like elements.

DETAILED DESCRIPTION

Attention is first drawn to FIGS. 1A and 1B illustrating an embodiment of a capsulotomy device 10 of the present invention in, respective, assembled and exploded states. Capsulotomy device 10 in these views may be seen including the following main members: a base 12, a blade holder 14, a piston 16 and a driving mechanism 18.

Capsulotomy device 10 may be used for cutting with a cutting blade, held by the blade holder, a portion of an anterior side of a lens capsule during e.g. cataract surgery. Prior to performing such cutting action, the capsulotomy device may be advanced towards the lens capsule by first placing a tip region 121 at a distal portion of the base through an incision (e.g. a 2.2 mm incision providing a corneal access) formed in a cornea of an eye to be treated (eye anatomy, e.g. cornea and lens capsule, not shown).

It is noted that the directional term 'distal' and its opposite term 'proximal' (and their derivatives), which are used herein; generally refer to, respective, remoteness or proximity to a person e.g. physician or surgeon, handling various embodiments of capsulotomy devices of the invention in their assembled state(s). In addition, the terms 'up' and 'down' (and their derivatives) refer to general directions existing in relation to the described embodiments, when held in an orientation suitable for performing a surgical procedure.

Blade holder 14 in this example may be arranged to include a rod 141, a tube 142 and a cutting blade 143. Tube 142 at its distal end may be arranged to have a downwardly projecting pivot 1421 (see pivot 1421 e.g. in FIG. 4B). The cutting blade 143 in turn may be arranged to be pivotally coupled to pivot 1421. Rod 141 may be arranged to pass through the tube to extend up to a distal area of the holder where it may couple to the blade (see coupling between rod and blade e.g. in FIG. 6).

Piston 16 may include a handle 161 at a proximal region and a shaft 162 that extends away from the handle in a distal direction up to a distal end of the piston. The shaft in this example includes a passage 163 that extends therethrough and opens out of the piston at its distal end. Passage 163 in this example may have a canal-like formation opening radially out of the shaft here in an upward direction, besides at a distal portion 164 of the shaft where the canal-like formation is concealed from above.

In an assembled state of the capsulotomy device, a proximal portion 144 of tube 142 may be fixed within the shaft's distal portion 164 leaving the rod 141 at its proximal end projecting into the canal-like portion of passage 163. Piston 16 may include in addition at the shaft's distal portion 164 an axle 165 that projects in this example radially upwards in the same direction towards which the canal-like portion of passage 163 opens.

The driving mechanism 18 in this embodiment may have a manually driven rotary-like formation including a driving wheel 181, a bar 182 and a grip 183. Driving mechanism 18 in an assembled state of the capsulotomy device may be arranged to have its driving wheel 181 pivotally coupled to axle 165 with its grip 183 slidably located within passage 163 and securely gripping onto the proximal end of rod 141.

Bar 182 may be coupled at a general distal side thereof via a link 99 (see 'dashed-circle' marked in FIG. 5 and indicated by numeral 99 in FIG. 5A) to a relative outer radial portion of the driving wheel and at a general proximal side thereof to grip 183. Thus, by rotating driving wheel 181 about axle 165, grip 183 via bar 182 may be arranged to slide back and forth within passage 163 urging the rod 141 that is attached thereto to move back and forth within tube 142 that accordingly remains fixed at its proximal region 144 to the piston's distal region 164. Such back and forth movements of rod 141 may be arranged to activate rotation of the cutting blade about its pivot as will be described below.

Base 12 extends along a longitudinal axis X defining also a longitudinal axis of the capsulotomy device in its assembled state. Base 12 may have a loading chamber 122 proximal to its tip region 121, and a pathway 123 extending therethrough along axis X that passes through loading chamber 122 and tip region 121 to open out of the device at its distal end. In this shown example, pathway 123 may have a proximal duct-like portion that opens upwards. The duct-like portion here extends from a proximal end of the base and up to the loading chamber.

Formation of an assembled state of the capsulotomy device may be assumed as following. First a sub-assembly may be formed including the fitted together piston 16 and blade holder 14 with driving mechanism 18 coupled to both. This sub-assembly may then be placed with the cutting blade 143 located within loading chamber 122 and portions of shaft 162 and blade holder 14 received and/or located within pathway 123, here mostly within the duct-like portion of the pathway. Loading chamber 122 may include an upper movable lid that may be removed for placing cutting blade within the loading chamber and then re-attached to close the loading chamber from above.

Figure 2B:
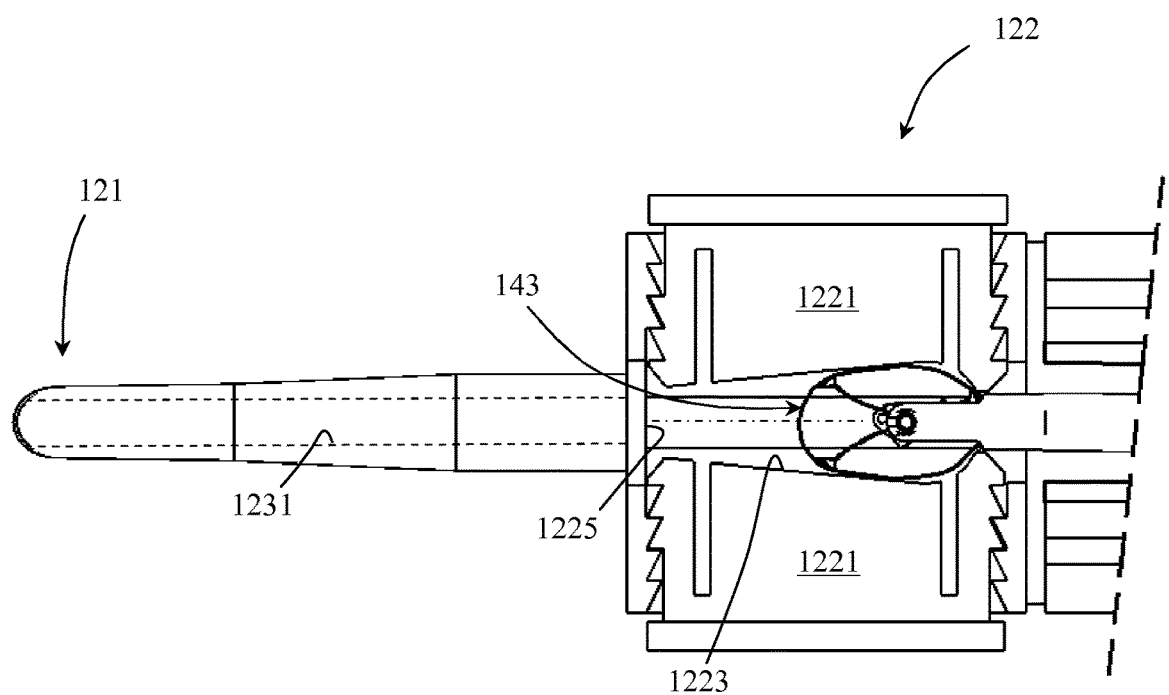

For a better view of the loading chamber 122 attention is now drawn to FIGS. 2A and 2B. The capsulotomy device prior to being used in a surgical procedure, e.g. when in storage, may be arranged to include its cutting blade within a central open area 1222 of the loading chamber as seen in FIG. 2A. The loading chamber includes bearing members 1221 located on both lateral sides of open area 1222.

In an un-loaded state of the loading chamber, the bearing members 1221 are located in respective retracted positions, permitting formation of the open area 1222 where the cutting blade 143 rests in a free non-distorted and/or compressed state. This un-loaded state can be seen in FIG. 2A. The cutting blade, typically formed from elastic material such as nitinol, may be urged to assume a generally compressed profile by urging the bearing members 1221 inwards to thereby assume the loaded state generally seen in FIG. 2B. This loaded state here shown may be defined as providing a so-called 'initial deformation' in the cutting blade, where later further deformation in this shown example may be assumed while the cutting blade is injected downstream out of the loading chamber on route to exit the device at its distal end.

Each bearing member 1221 in this illustrated example includes a bearing face 1223 facing towards the cutting blade into central open area 1222; and a pair of resilient arms 1224 on both axial sides of the member. The resilient arms are possibly arranged with angled teeth engaged with respective teeth formed in an outer housing of the loading chamber to form a ratchet-like formation that permits motion of each bearing member in this example only towards the cutting blade.

The bearing face 1223 of each bearing member as here seen may be arranged to follow a general contour that tapers towards axis X in the distal direction—thus forming in the loaded state a general funnel shape leading towards an exit 1225 from the loading chamber.

Exit 1225 forms an entry from the loading chamber into a terminal distal portion 1231 of pathway 123 that passes through tip region 121. Through distal portion 1231 the cutting blade, initially compressed in the loaded state of the loading chamber, passes while undergoing further compression on route to exit the device's tip region and assume an operative state of the capsulotomy device suitable for performing cutting actions. In the operative state when located outside at the distal side of the device—the cutting blade flexes back to its general circular shape.

Figure 3:
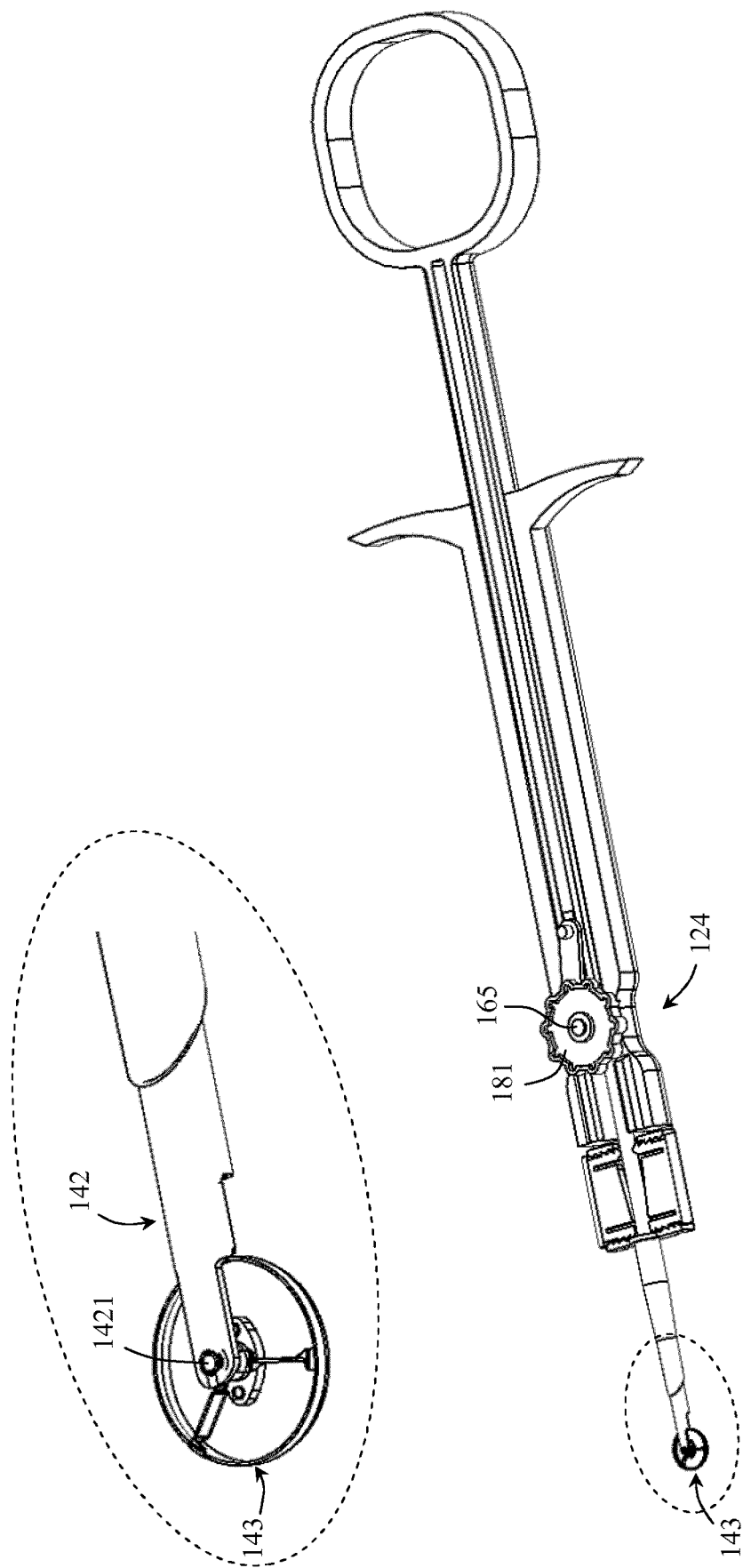
FIG. 3 schematically shows a perspective view of an embodiment of a capsulotomy device in an operative state.

Attention is drawn to FIG. 3 illustrating the capsulotomy device in an operative state after the cutting blade has exited the tip region. As seen in the enlarged section at the top of the figure, the cutting blade remains accordingly pivoted to pivot 1421 at the distal end of the tube 142. Also, as can be seen; in the operative state of the capsulotomy device—the driving wheel 181 may reach a recessed region 124 along base 12 permitting tactile access to the driving wheel for manual manipulation of the driving wheel about axle 165.

Figure 4A:
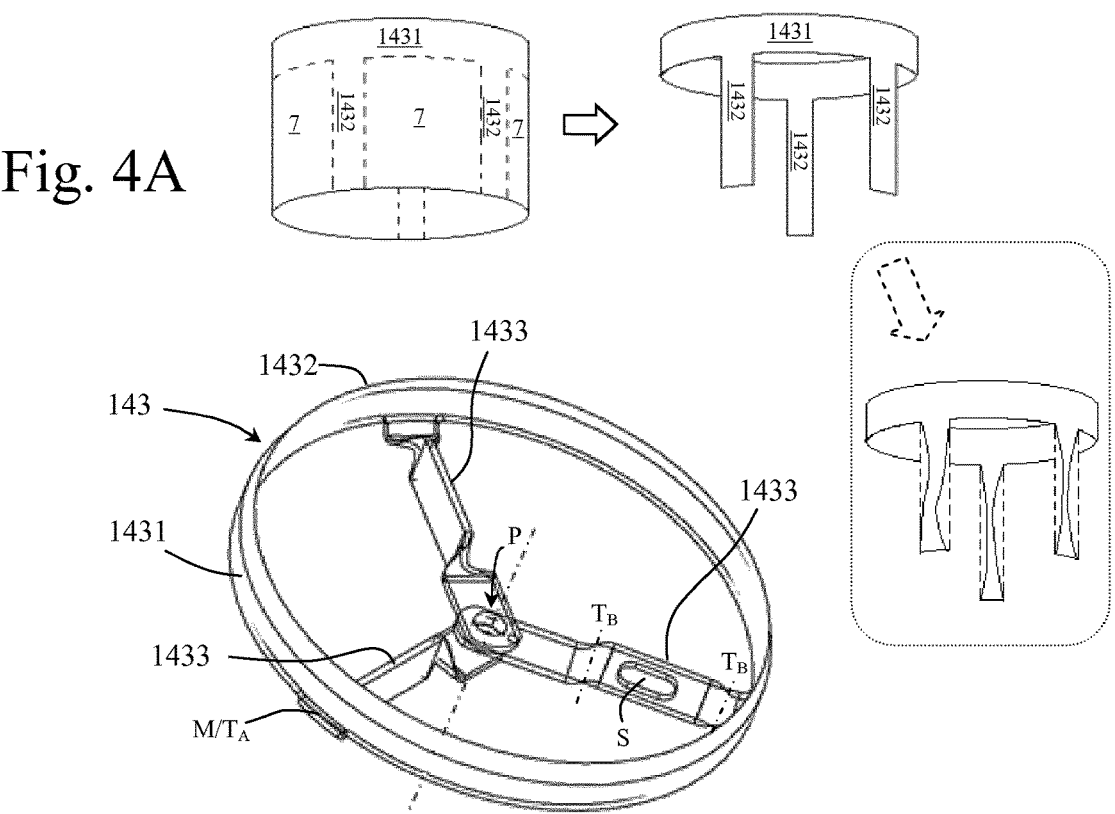
FIG. 4A schematically shows possible processing steps that may be taken to form an embodiment of a cutting blade from a cylindrical piece of material.
Figure 4B:
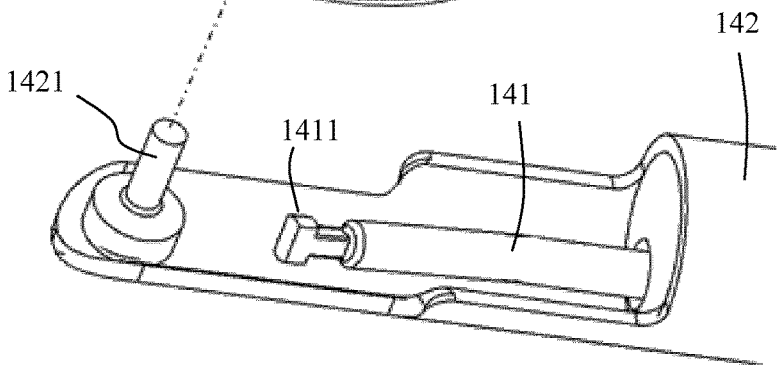
FIGS. 4B and 4C schematically show exploded and non-exploded perspective bottom views of a distal portion of an embodiment of a capsulotomy device.
Figure 4C:
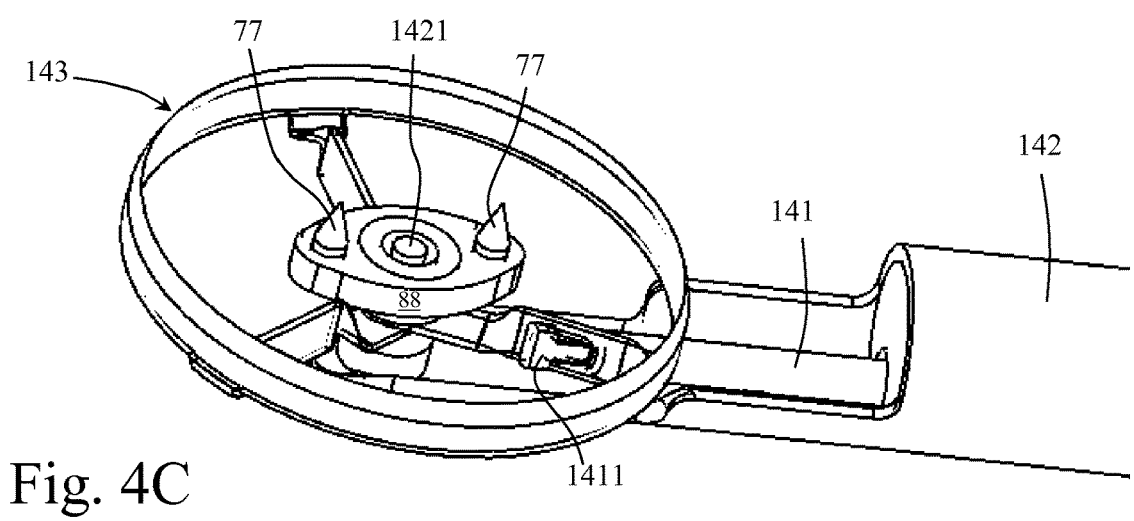

Attention is additionally drawn to FIGS. 4B and 4C providing a perspective bottom view of a distal region of the capsulotomy device. As seen in this view, cutting blade 143 may be arranged to have a circular body 1431 including a cutting edge 1432 extending along a lower counter thereof. Cutting blade 143 in addition may include several spoke members 1433, here three spoke members, that extend each away from a respective merge M along an upper side of the blade's body 1431.

With attention additionally drawn to FIG. 4A an embodiment of a cutting blade 143 will be discussed. Cutting blade 143 in this embodiment may be formed by first providing a generally cylindrical piece of material (e.g. nitinol) and then cutting away excess material 7 from the material to leave a skeleton of remaining material that includes material for the blade's body 1431 and the blade's spoke members 1433. Further machining may then be performed e.g. to form the cutting edge at the lower side of body 1431 (etc.) and each spoke member may then undergo several twists, here three twist actions resulting in formation of three twist regions T in each spoke.

As shown by within the dotted rectangle and the dashed arrow at the right hand side of this figure, each spoke member may undergo cutting to form twist regions therein, here optionally formed by the remaining curved formation of each spoke member after such cutting. As discussed herein, said twist regions may in addition or alternatively be formed in other manners e.g. by bending spoke members.

With attention drawn back to FIGS. 4B and 4C, a first one of the twist regions $T_A$ may be seen located at the merge M where each spoke member merges with the blade's body and two additional twist regions $T_B$ may be located along each spoke member. Each spoke member 1433 may include an aperture at its end most distal of body 1431 and the bending and twisting of each spoke member (away from the position illustrated at the right-hand side of FIG. 4A) may be such that all apertures align at a central region of the blade's body to form a pivoting aperture P of the blade.

The twist regions $T_B$ formed along each spoke member may be said to define each a general twist axis extending generally parallel to an axis about which the blade's body 1431 is formed. Thus, provision of the twist regions $T_B$ along such orientations may be adapted to facilitate compression of the cutting blade to a general compressed (possibly elliptical) shape permitting passage of the cutting blade via the terminal distal portion 1231 or when still in the loading chamber.

Coupling of rod 141 with the cutting blade as seen in FIGS. 4B and 4C may be provided as following. One of the spoke members 1433 may be defined as an 'activation spoke' provided with a slit S formed therethrough. Rod in turn may be formed at its distal end with a hook-like formation 1411. Coupling may thus be formed by inter-engaging hook 1411 within slit S—so that urging rod back and forth may result in oscillating the cutting blade to rotate about its pivot via interaction with the 'activation spoke'.

With attention drawn to FIG. 4C, cutting blade 143 may be seen pivotally coupled at its aperture P to pivot 1421. To pivot 1421 may additionally be fixed one or more anchoring pins 77. The anchoring pins 77, in this example two such pins, may be fitted to a plate 88 that includes a general elliptical profile suited for passage together with the cutting blade via terminal distal portion 1231.

In fact—in embodiments including such pin(s) and in particular plate 88—compression of the cutting blade may be up to plate 88, which is located within the blade. Provision of such pin(s) may permit so-called anchoring of the cutting blade against the lens capsule during a surgical procedure—so as to assist in performing the cut through the capsule.

Figure 5A:
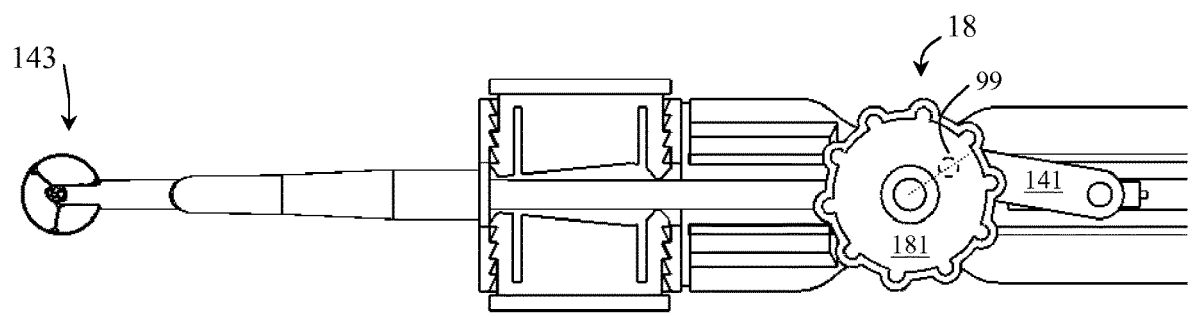
FIGS. 5A to 5C schematically show top views of an embodiment of a capsulotomy device in its operative state, during various states of actuation.
Figure 5B:
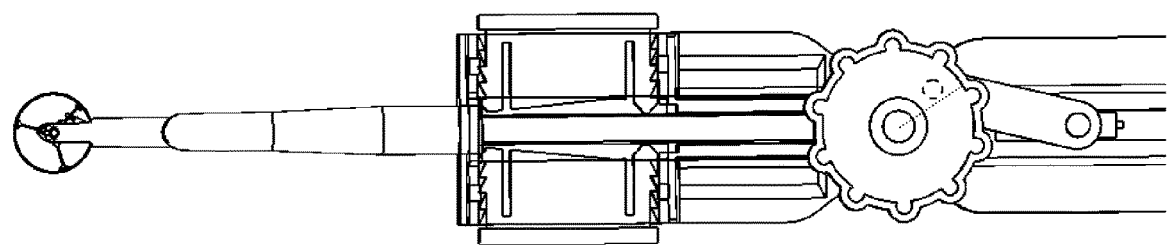
Figure 5C:
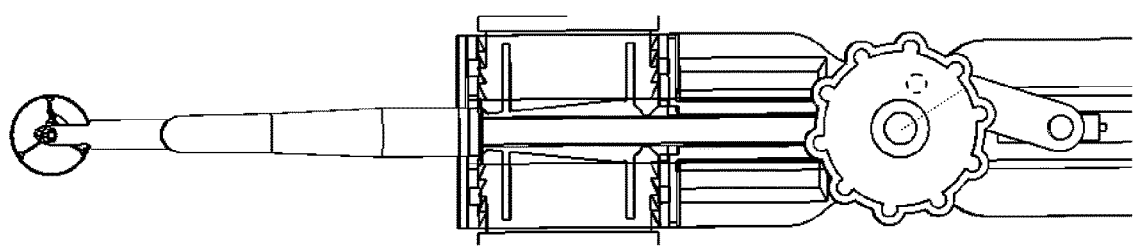
Figure 6A:
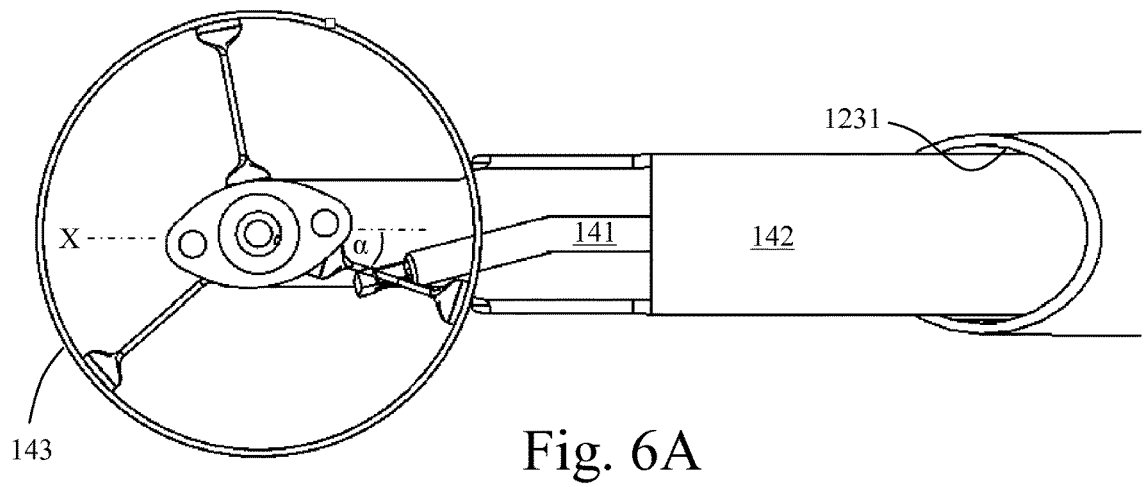
FIGS. 6A to 6C schematically show enlarged bottom views of a cutting blade at a distal portion of the capsulotomy device of FIG. 5 during actuation states corresponding to the respective actuation states seen in FIGS. 5A to 5C.
Figure 6B:
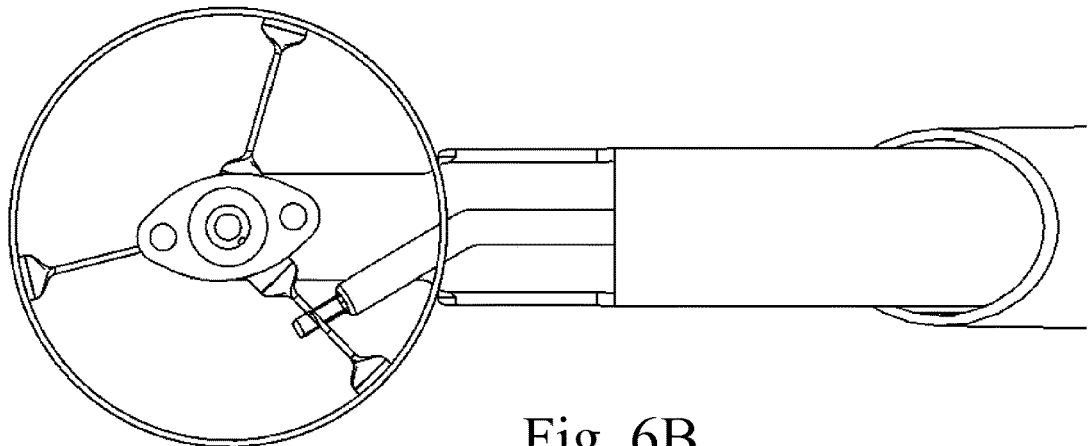
Figure 6C:
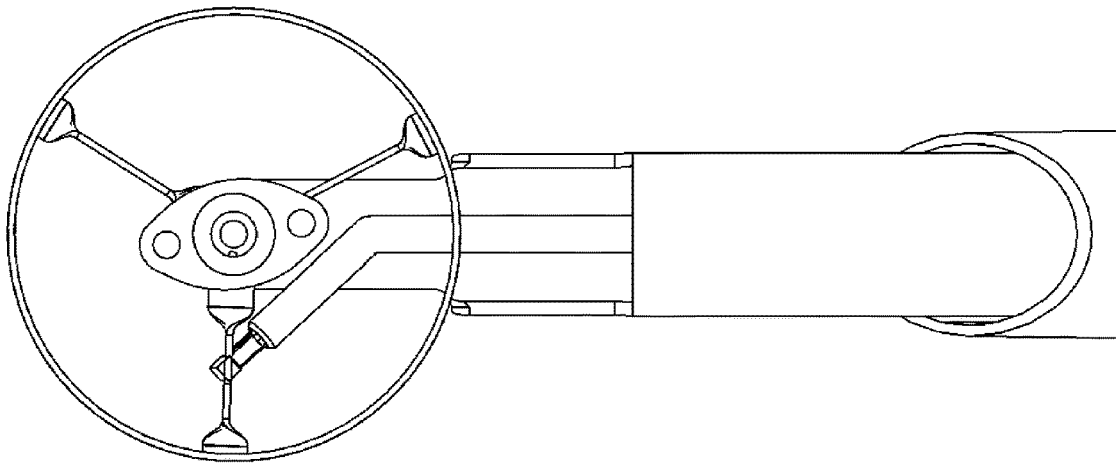

Attention is drawn to FIGS. 5A to 5C and to the respective FIGS. 6A to 6C to discuss activation of driving mechanism 18 and its effect on the rotational orientation of cutting blade 143 about its pivot. In FIG. 5A, an initial 'home' position of driving wheel 181 about axle 165 is seen. The dotted line provided in FIGS. 5A to 5C and maintained to have the same angular positions throughout these figures, passes in FIG. 5A through the location where link 99 connecting bar 182 to driving wheel 181 is located.

FIG. 6A provides a view of cutting blade that corresponds to the 'home' position of driving mechanism in FIG. 5A.

Rod 141 in this 'home' position may be at a retracted proximal position maintaining the cutting blade in a respective 'home' position in which the 'activation spoke' coupled to the rod may be generally aligned with or at a relative small angle α (preferably smaller than 20 degrees) to axis X.

In this 'home' position, the spoke members are angularly arranged to permit suitable compression (inter alia via their respective twist regions $T_B$) for obtaining the required compressed profile needed when distally advancing of the cutting blade through the distal portion 1231 of pathway 123 or while retracting the cutting blade via same distal portion 1231 e.g. after completion of a surgical procedure.

FIGS. 5B and 5C illustrate further rotation of driving wheel, here in a counter clockwise direction as can be seen by transitions in the location of link 99 acting here as a so-called marker indication amount of rotation relative to the dotted line that remains fixed in its angular orientation. The effect that such further rotation may have on the cutting blade can be seen in FIGS. 6B and 6C, respectively.

FIG. 6B exemplifies that a further incremental rotation of the driving wheel (from the position in FIG. 5A to that in FIG. 5B) advances rod 141 slightly further in the distal direction and consequently urges further rotation of the cutting blade. In FIG. 6C a yet further incremental rotation of the driving wheel (from the position in FIG. 5B to that in FIG. 5C) advances rod 141 yet further in the distal direction, thus further urging rotation of the cutting blade. Oscillating the driving wheel back and forth about its axle may thus urge a corresponding oscillation of the cutting blade about its pivot.

Figure 7A:
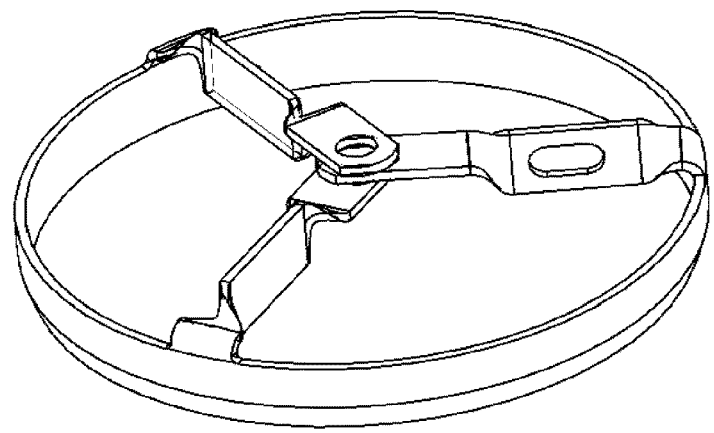
FIGS. 7A and 7B schematically show various cutting blade embodiments suitable for use with the various capsulotomy device disclosed.
Figure 7B:
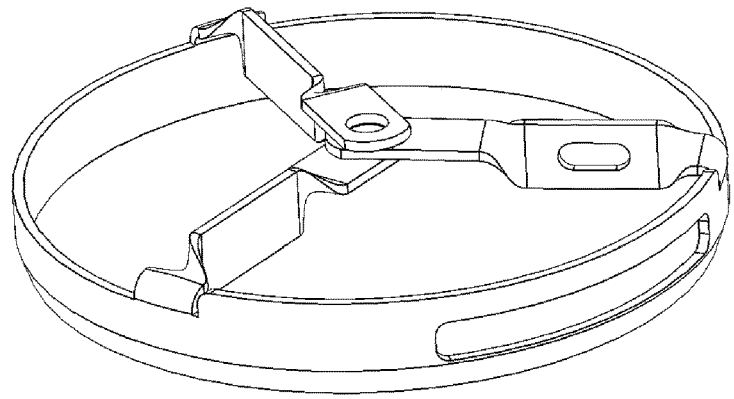

Attention is drawn to FIGS. 7A and 7B illustrating in FIG. 7A an embodiment of the cutting blade generally similar to that already discussed hereinabove and in FIG. 7B an embodiment of a cutting blade generally similar to the one discussed but with a wider body that includes an arc shaped slit through which the rod can pass on its way to reach and couple with the 'activation spoke'.

Figure 8:
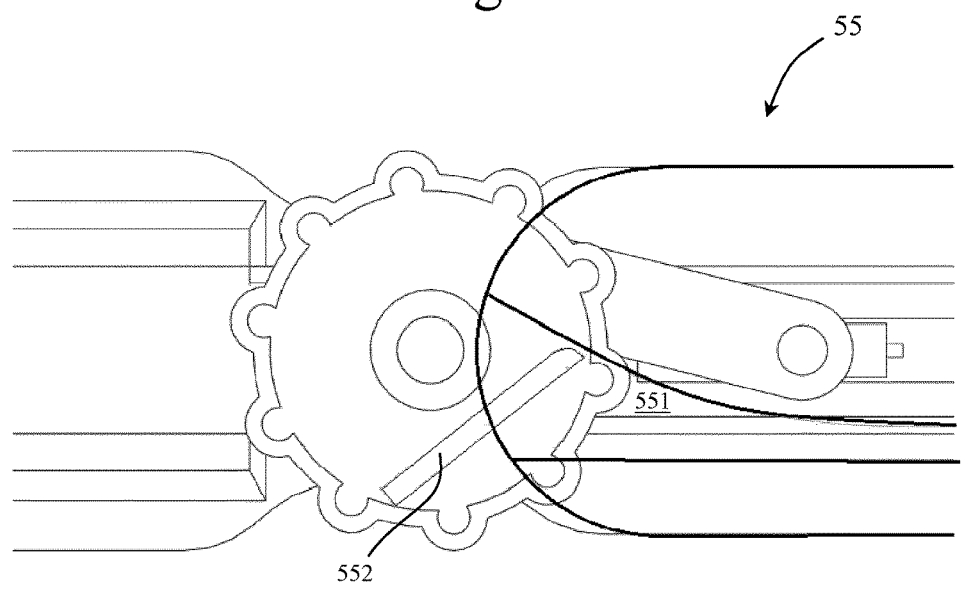
FIG. 8 schematically shows an embodiment of a guide for guiding various capsulotomy device embodiments away from their operative states.

FIG. 8 provides a view exemplifying one option of a guide 55 suitable for ensuring that the drive wheel may be guided to its 'home' position when attempting to retreat the cutting blade back through passageway 1231. Guide 55 in this example may be in the form of a cover placed proximal to the location where the driving mechanism is positioned when activating rotation at the cutting blade. Guide 55 may be provided with a key way 551 and drive wheel is provided with key 552.

Retracting piston in the proximal direction may in this example urge key 552 to engage key way 551 that consequently guides and urges the driving wheel to rotate and align towards its 'home' position thus also urging the cutting blade towards its 'home' position (seen in FIG. 6A) suitable for retraction via passageway 1231.

Figure 9A:
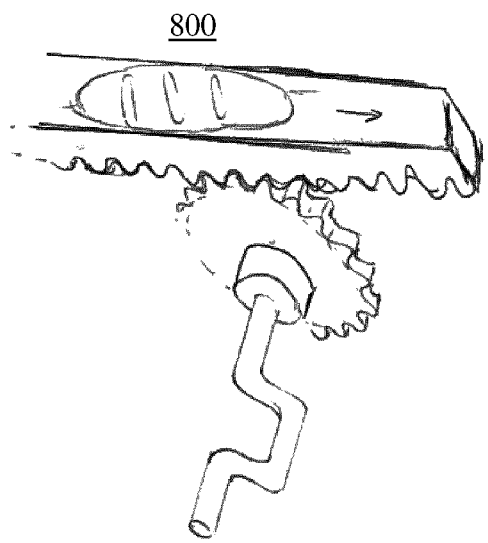
FIGS. 9A to 9C schematically show various driving mechanisms possibly used with the various capsulotomy device embodiments disclosed.
Figure 9B:
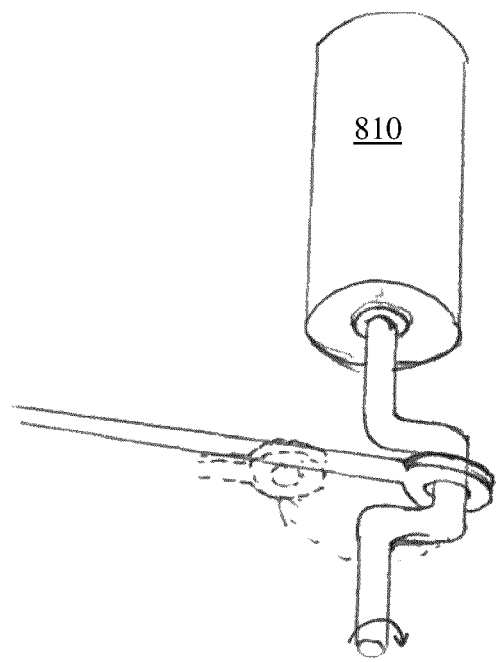
Figure 9C:
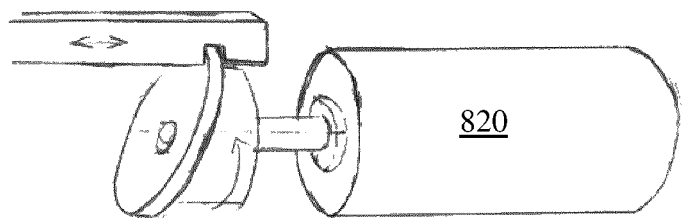

Attention is drawn to FIG. 9A to 9C illustrating various driving mechanisms suitable for urging rotating and/or oscillation of the cutting blade other than the discussed driving mechanism 18. FIG. 9A illustrates an example of a slider 800 arranged for transferring linear movement to rotational reciprocating movement via a crankshaft to the cutting blade e.g. via means of a rod generally similar to rod 141 discussed herein.

FIG. 9B illustrates an example of use of a driving mechanism in form of a motor 810 e.g. a DC motor for urging reciprocating movements in a cutting blade here via a crankshaft. FIG. 9C illustrates an example of use of a driving mechanism in form of a DC motor or solenoid 820 for urging reciprocating movements in a cutting blade here via a slanted disc engaged with a rod such as rod 141.

Figure 10A:
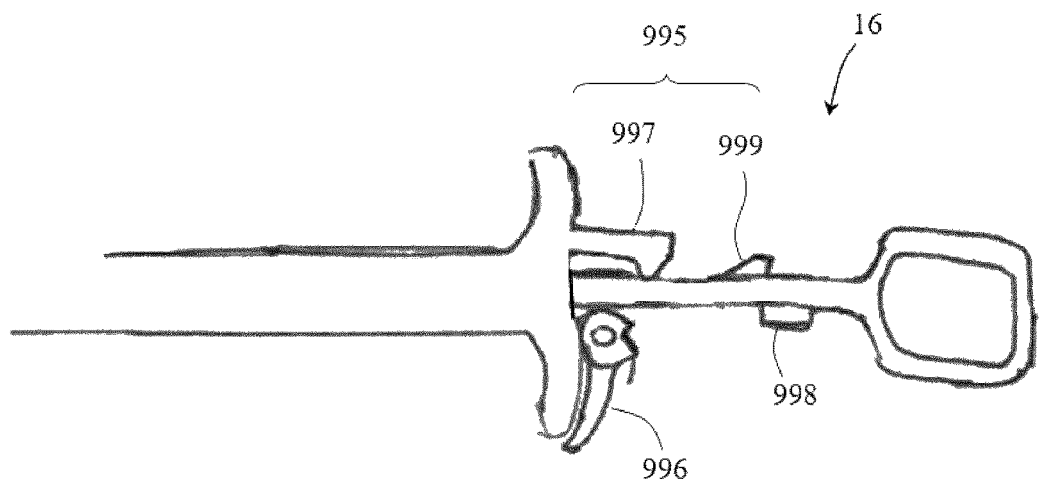
FIGS. 10A and 10B schematically show a proximal portion of an embodiment of a capsulotomy device illustrating a catch-mechanism suitable for reversibly locating the various capsulotomy device embodiments disclosed herein in respective operative states.
Figure 10B:
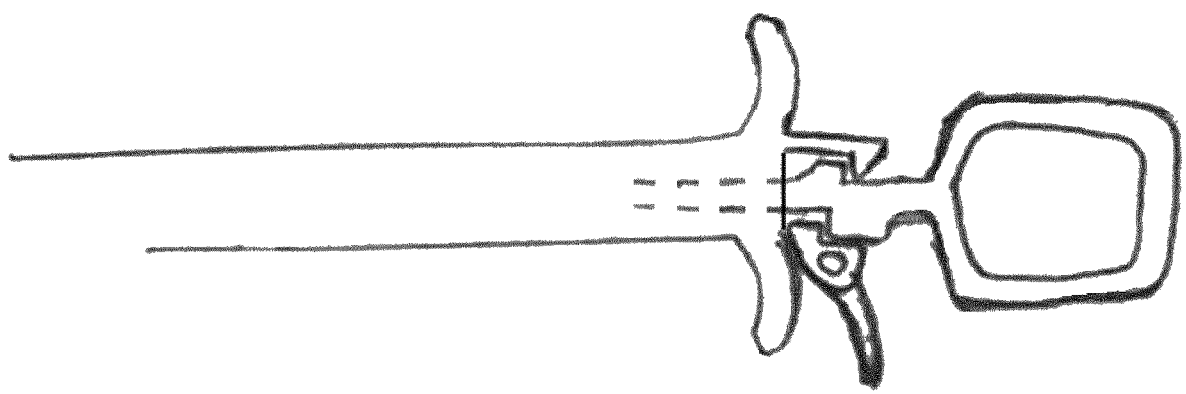

Attention is drawn to FIGS. 10A and 10B exemplifying a fixing mechanism 995 possibly used for ensuring that a defined fixed position may be reached during use of various capsulotomy device embodiments—where the capsulotomy device(s) may be in their respective 'operative' position(s) (seen e.g. in FIG. 5) suitable for performing a surgical cutting procedure.

In this example, piston 16 may include along its shaft a snap member 999 and a stop 998. When the piston may be urged in the distal direction (e.g., from the position seen in FIG. 1A to that in FIG. 3), snap member 999 may engage a snap arm 997 adapted to snap onto snap member 999 when engaged therewith. This snapping engagement between snap arm 997 and snap member 999 may define a state identifiable by a surgeon using the device that may indicate that the device reached its operative position suitable for performing a cutting action.

Once a surgical procedure has been completed, and in order to release the snapped state holding the device in its operative position, a surgeon may manipulate a lever 996 fixed e.g. to device's base, which may be adapted to move and bear back against stop 998 in the proximal direction to urge the piston away from the snapped state e.g. to the position seen in FIG. 2 where the cutting blade may be retreated to within the loading chamber or to any other position within and along pathway 123.

In at least certain embodiments, fixing mechanism 995 may be arranged to function by fingers of the same hand activating movement of the piston—so that e.g., to activate the lever 996 a surgeon handling the device may not need remove his hand from the location it otherwise would be in during normal use.

Figure 11:
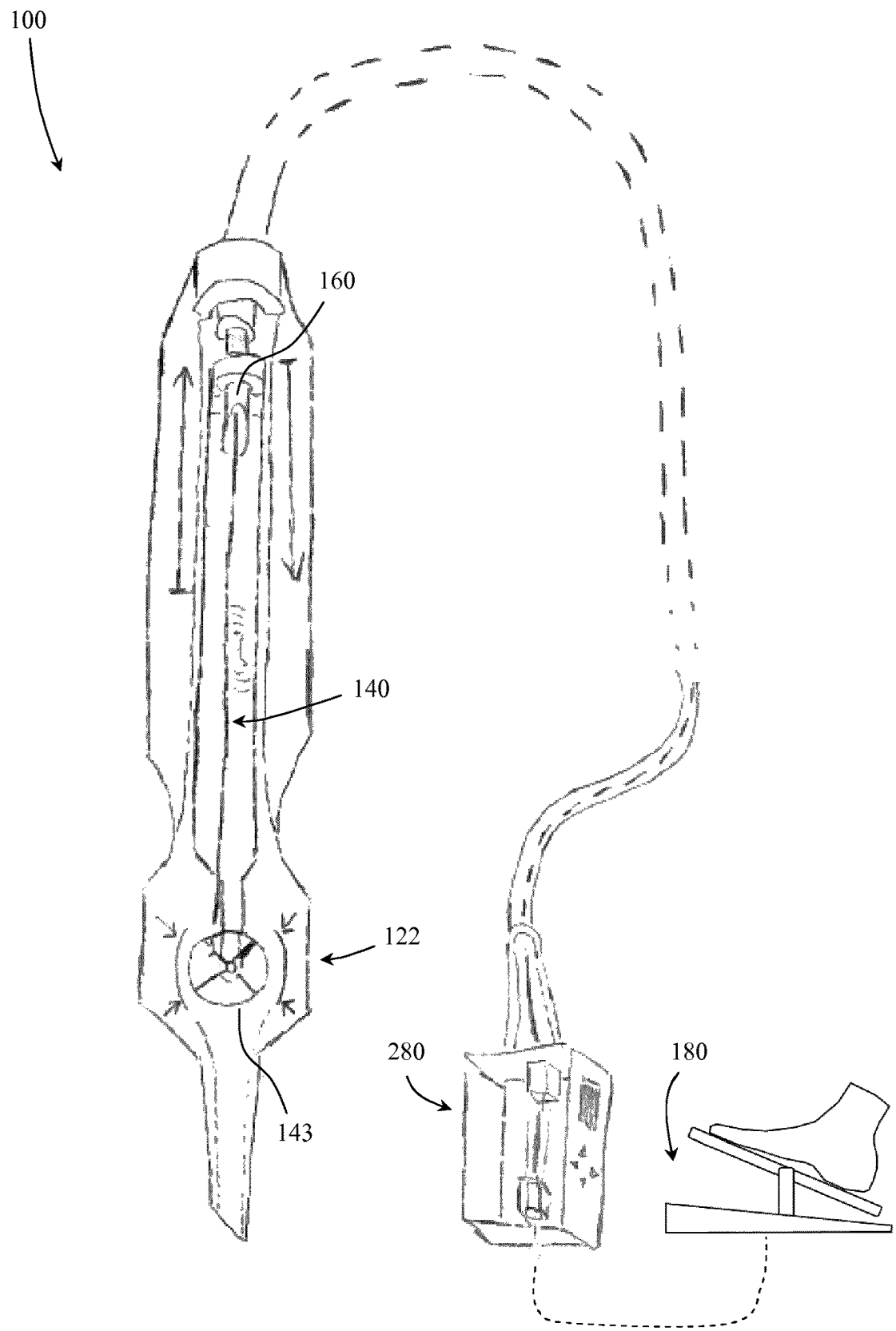
FIG. 11 schematically shows a capsulotomy device embodiment comprising an embodiment of a piston for urging the device towards and away from its operative state.

Attention is drawn to FIG. 11 illustrating an embodiment of a capsulotomy device 100 hand-piece that includes an actuated piston 160. Such hand-piece may be a of a one piece disposable type. Piston 160 in one example may be electrically actuated.

In a first actuated state, piston 160 may be arranged to urge the device's blade holder 140 in a distal direction so that the device assumes an operative position suitable for performing a cutting operation. In a second actuated state, piston 160 may be arranged to retract the device's blade holder 140 back in a proximal direction so that the device's cutting blade 143 is retracted back towards the device's loading chamber 122.

In FIG. 11 capsulotomy device 100 is shown in its retracted state. It is noted that piston 160 may be combined with driving mechanisms (such as those in FIGS. 9A and 9B) such that in addition to actuated extension and retraction of the device's blade holder, the reciprocating movements of the device's cutting blade may be also actuated (e.g. electrically actuated).

Actuation of piston 160 and/or driving mechanisms for urging oscillation may be activated via means such as a foot pedal 180 as illustrated in the figure. A possible control box 280 receiving inputs from the pedal may include electronic components that generate an electric impulse and/or output signal that may in turn be transferred to the hand-piece of the capsulotomy device 100. Toggles provided at the control box 280 may permit adjustment of the frequency of the oscillation (power of the impulse) and may permit plugging in or unplugging of different single use hand-pieces and/or different pedals.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

Further more, while the present application or technology has been illustrated and described in detail in the drawings and foregoing description, such illustration and description are to be considered illustrative or exemplary and non-restrictive; the technology is thus not limited to the disclosed embodiments.

Variations to the disclosed embodiments can be understood and effected by those skilled in the art and practicing the claimed technology, from a study of the drawings, the technology, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage.

The present technology is also understood to encompass the exact terms, features, numerical values or ranges etc., if in here such terms, features, numerical values or ranges etc. are referred to in connection with terms such as "about, ca., substantially, generally, at least" etc. In other words, "about 3" shall also comprise "3" or "substantially perpendicular" shall also comprise "perpendicular". Any reference signs in the claims should not be considered as limiting the scope.

Although the present embodiments have been described to a certain degree of particularity, it should be understood that various alterations and modifications could be made without departing from the scope of the invention as hereinafter claimed.

The invention claimed is:

1. A capsulotomy device comprising a tool holder, the tool holder comprising a circular cutting blade at a distal end of the tool holder and being arranged to move in a distal direction in the device to form an operative state of the device where the cutting blade projects out of a distal end of the capsulotomy device, wherein the tool holder comprising an axially extending rod that is connected at a distal axial end of the rod to the cutting blade and is adapted in the operative state to reciprocate in the distal and proximal directions to urge oscillating rotation of the cutting blade, and wherein the cutting blade comprising a circular body and a plurality of spoke members extending between a pivot of the cutting blade and coupled to the circular body, wherein the cutting blade comprises a circular cutting edge along a circumference of the body.

2. The capsulotomy device of claim 1, further comprising a piston and the tool holder being coupled to the piston at a proximal end of the tool holder, wherein the urging of the tool holder in the distal direction is via the piston.

3. The capsulotomy device of claim 2, wherein the piston is actuated to urge the tool holder in the distal direction.

4. The capsulotomy device of claim 2, wherein the piston is manually activated.

5. The capsulotomy device of claim 1, further comprising a driving mechanism for reciprocating at least portion of the tool holder in the distal and proximal directions.

6. The capsulotomy device of claim 5, wherein the driving mechanism is manually activated.

7. The capsulotomy device of claim 5, wherein the driving mechanism is automatically activated.

8. The capsulotomy device of claim 1, wherein the tool holder comprises an outer tube and the rod extending through the tube.

9. The capsulotomy device of claim 8, wherein the cutting blade being pivoted to a distal end of the tube.

10. The capsulotomy device of claim 8, wherein a proximal end of the rod being coupled to a driving mechanism.

11. The capsulotomy device of claim 1, further comprising a loading chamber, and prior to assuming the operative state of the device the cutting blade is compressed in the loading chamber.

* * * * *